(12) United States Patent
Schmotzer

(10) Patent No.: US 6,290,700 B1
(45) Date of Patent: Sep. 18, 2001

(54) DEVICE FOR STIFFENING AND/OR CORRECTING A VERTEBRAL COLUMN OR SUCH LIKE

(75) Inventor: Hans Schmotzer, Aarau (CH)

(73) Assignee: Plus Endoprothetik AG, Rotkreuz (CH)

( * ) Notice: Subject to any disclaimer, the term of this patent is extended or adjusted under 35 U.S.C. 154(b) by 0 days.

(21) Appl. No.: 09/485,043
(22) PCT Filed: Jul. 31, 1998
(86) PCT No.: PCT/EP98/04812
§ 371 Date: Apr. 25, 2000
§ 102(e) Date: Apr. 25, 2000
(87) PCT Pub. No.: WO99/05980
PCT Pub. Date: Feb. 11, 1999

(30) Foreign Application Priority Data

Jul. 31, 1997 (DE) .............................................. 197 33 160
Sep. 5, 1997 (DE) .............................................. 197 38 968

(51) Int. Cl.[7] .................................................... A61B 17/56
(52) U.S. Cl. ................................ 606/61; 606/69; 606/73; 606/72
(58) Field of Search .................................. 606/61, 60, 54, 606/55, 56, 57, 58, 59, 62, 63, 70, 71, 72, 73

(56) References Cited

U.S. PATENT DOCUMENTS 4,950,269 * 8/1990 Gaines, Jr. .............................. 606/61
5,042,982 * 8/1991 Harms et al. ........................... 606/61
5,190,543 * 3/1993 Schlapfer ................................ 606/61
5,683,390 * 11/1997 Metz-Stavenhagen et al. ....... 606/61
5,873,878 * 2/1999 Harms et al. ........................... 606/61

FOREIGN PATENT DOCUMENTS

669109 * 8/1995 (EP) ...................................... 606/61

* cited by examiner

Primary Examiner—Pedro Philogene
(74) Attorney, Agent, or Firm—Knobbe, Martens, Olson & Bear, LLP

(57) ABSTRACT

An apparatus for supporting and correcting a skeletal structure includes at least two anchoring elements for a connecting element. The connecting element includes an elongate tensioning element that can be fixed to the anchoring element. Spacer sleeves can be slid over the tensioning element in order to keep adjacent anchoring elements a predetermined distance apart when a pulling force is applied to the tensioning element. Each anchoring element is attachable to a bone or vertebra. Surfaces of the anchoring elements against which the spacer sleeves abut are spherically curved. An end face at an end of each spacer sleeve towards the anchoring element has a shape complementary to an associated supporting surface of the anchoring element. The anchoring element has a passage for the tensioning element, wherein entrance and exit openings of the passage passing through the anchoring element each expand outward on all sides in a conical or trumpet-like shape.

17 Claims, 2 Drawing Sheets

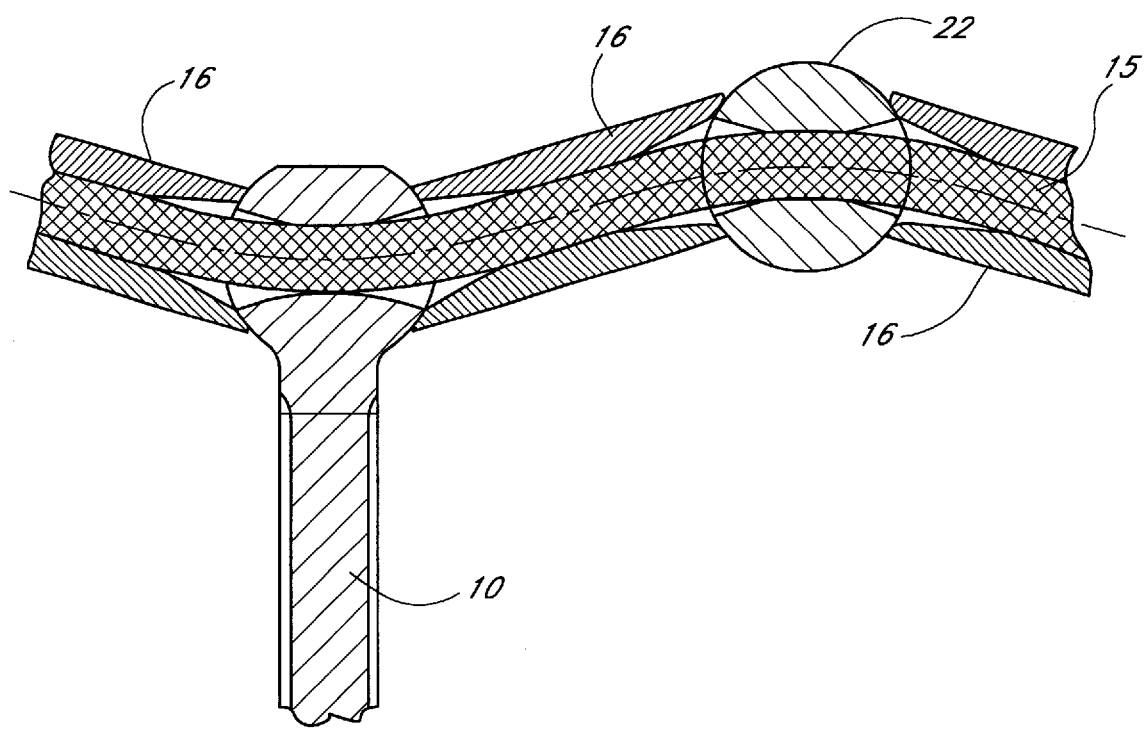
FIG.2
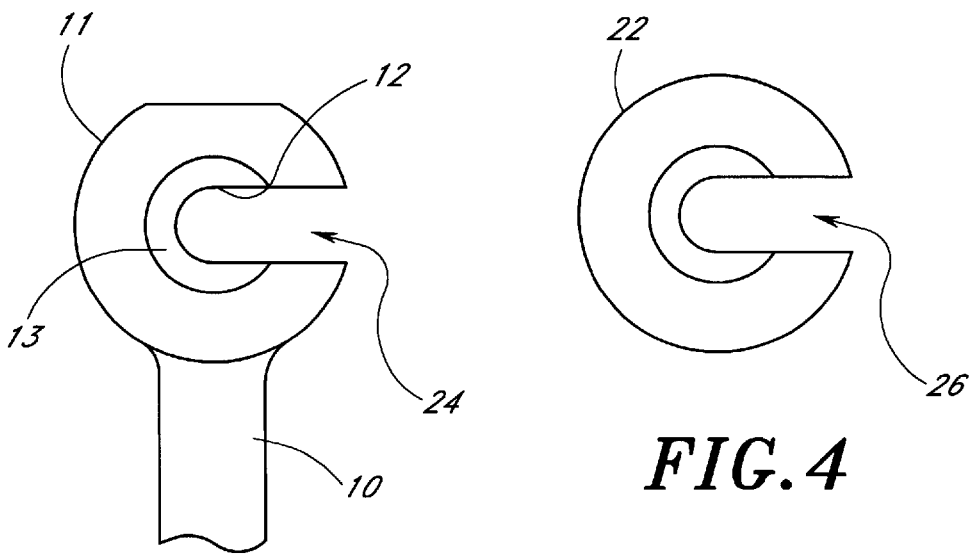
FIG.3  FIG.4

DEVICE FOR STIFFENING AND/OR CORRECTING A VERTEBRAL COLUMN OR SUCH LIKE

FIELD OF THE INVENTION

The invention relates to an apparatus for stiffening and/or correcting a skeletal structure or section thereof consisting of at least two bones or bone fragments, or a section of the spinal column consisting of at least two vertebrae, with at least two anchoring elements each of which can be attached to a bone or vertebra to receive a connecting element comprising a tensioning means in the form of a cable, wire or rod, which can be attached to the anchoring element, and spacer sleeves that can be slid over the tensioning means so that when a pulling force is exerted on the tensioning means, adjacent anchoring elements are kept a predetermined distance apart.

BACKGROUND OF THE INVENTION

An apparatus of this kind is known from WO 94/17745 in connection with the correction of a section of the spinal column. This known apparatus is characterized by high flexibility combined with long-term functional reliability. It can also be implanted by simple surgical techniques and allows subsequent adjustments of its positioning.

The object of the present invention is to improve the known apparatus with respect to its flexibility.

SUMMARY OF THE INVENTION

This object is achieved with an apparatus for stiffening and/or correcting a skeletal structure having at least two anchoring elements for a connecting element that has an elongate tensioning means and spacer sleeves. The spacer sleeves can be slid over the tensioning means in order to keep adjacent anchoring elements a predetermined distance apart when a pulling force is applied to the tensioning means. Each anchoring element is attachable to a bone or vertebra. Surfaces of the anchoring element against which the spacer sleeves abut are curved in a spherically convex or concave shape. As a result, it is possible for the abutment of the spacer sleeves against the associated anchoring elements to be adjusted to suit the direction of the tensioning means between two adjacent anchoring elements. Accordingly, it is not absolutely necessary for the tensioning means to be disposed at a predetermined angle with respect to the anchoring element. Instead, the operator can set this angle individually without being hindered by the spacer sleeves and their abutment against the anchoring elements.

Preferably the end surface of each spacer sleeve that faces an anchoring element is so formed as to be complementary to the supporting surface of the anchoring element, i.e. is spherically concave or convex. This measure ensures a large-area abutment of the spacer sleeves against the convex or concave curvature of the supporting surfaces of the anchoring elements.

An especially preferred embodiment of the apparatus in accordance with the invention is characterized in that the head of the anchoring element, which projects out of the bone or vertebra, is spherical in shape, in which regard it should be mentioned that the anchoring element can be either a pedicle screw or a pedicle hook. In the first case the head of the pedicle screw is a ball head.

So that the tensioning means can be fixed to the anchoring elements, the latter or their heads each comprise a passage, in particular a bore, with conical or trumpet-shaped, outwardly expanding openings through which the tensioning means is inserted or emerges. As a result, the tensioning means can enter or emerge from the anchoring element in an unconstrained manner, within a predetermined solid angle of 15 to 25 degrees.

In one advantageous embodiment the passage or bore is accessible over its entire length, either by way of a slot or by being openable, so that the tensioning means can be inserted into the passage in a direction perpendicular to the long direction of the passage. In both embodiments the anchoring element can first be fixed to the associated bone or vertebra. Only after this has been done is the tensioning means together with spacer sleeves attached to the anchoring elements. That is, in this embodiment the anchoring elements need not be threaded onto the tensioning means in advance. An especially simple embodiment is the first-mentioned, in which along the entire length of the passage in the anchoring element there is a slot through which the tensioning means is introduced. Alternatively, the anchoring element is constructed in two or more parts, such that the passage in the anchoring element can be opened over its entire length for insertion of the tensioning means. Thereafter the "lid" is replaced on the passage, so that the latter is closed radially on all sides.

The passages in the spacer sleeves preferably comprise entrance or exit openings that expand outward conically or in a trumpet shape, so that in the region where the spacer sleeves abut against the associated anchoring element, it is ensured that the tensioning means can run from the spacer sleeve into the passage through the anchoring element, and conversely, without constraint.

In another variant of the apparatus in accordance with the invention supporting balls that can be placed onto the tensioning means can also be provided, in particular balls slotted longitudinally, each of which can be inserted between two spacer sleeves in order to enable the distance between the anchoring elements to be altered or adjusted by placing in series two or more spacer sleeves of the same or different length. The said supporting balls each comprise a passage corresponding to the passage in the anchoring elements, to receive the cable-, wire- or rod-shaped tensioning means. The supporting balls are thus threaded onto the tensioning means, each between two adjacent spacer sleeves.

In order to increase versatility still further, it is conceivable to mount the part of each anchoring element that holds the tensioning means, in particular the ball head of a ball-head pedicle screw, so that it can rotate about an axis perpendicular to the longitudinal direction of the tensioning means, or about the long axis of the pedicle screw. As a result, the operator has an opportunity to adjust the tensioning means and the associated spacer sleeves in three dimensions, depending on the requirements of the individual case.

BRIEF DESCRIPTION OF THE DRAWINGS

In the following, a preferred embodiment of an apparatus in accordance with the invention is explained with reference to the attached drawings.

FIG. 2 is a sectional view to show the interplay between an anchoring element, tensioning means, supporting balls and spacer sleeves.

FIG. 3 is a sectional view of an anchoring element with a ball head having a slot.

FIG. 4 is a sectional view of a supporting ball having a slot.

DETAILED DESCRIPTION OF CERTAIN EMBODIMENTS OF THE INVENTION

Figure 1:
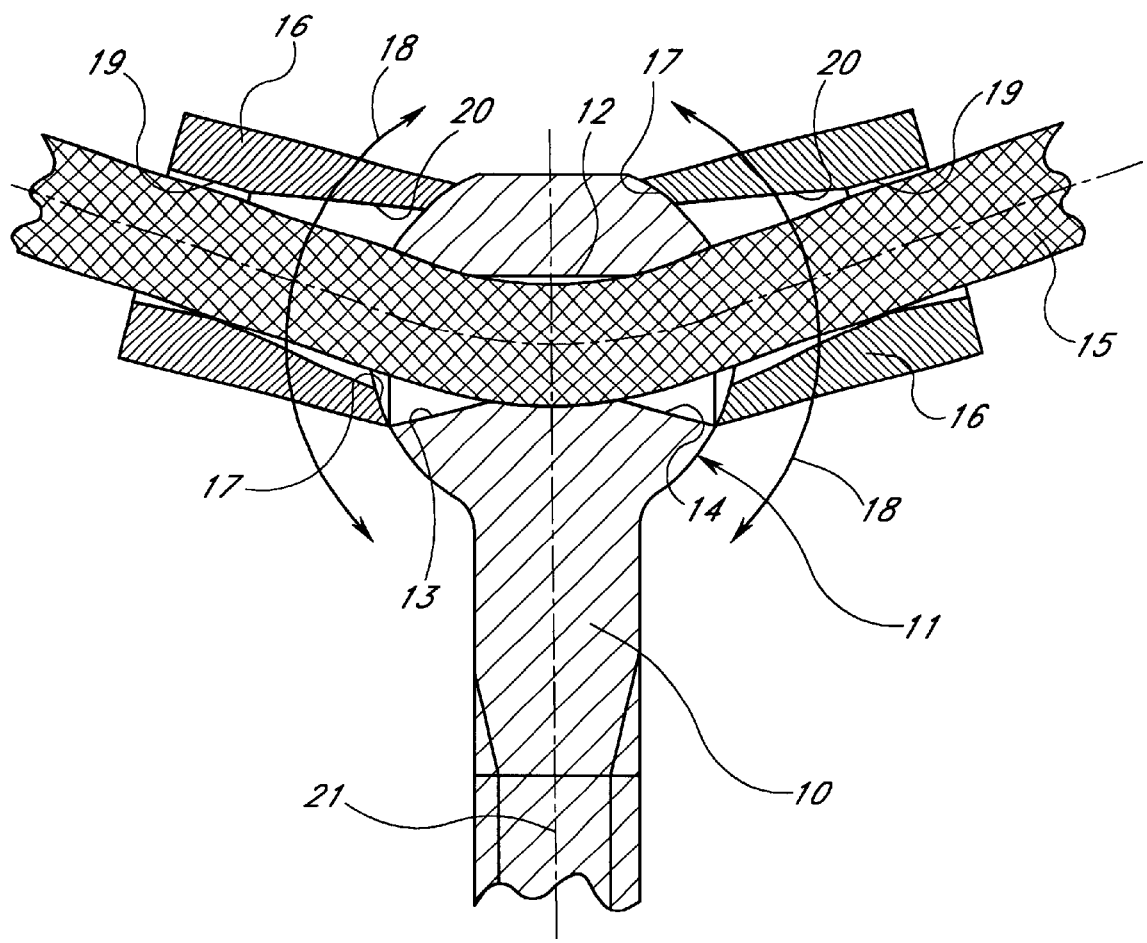
FIG. 1 is a sectional view to show the interplay between an anchoring element, tensioning means and spacer sleeves.

The reference numeral 10 identifies the anchoring part of a pedicle screw that can be screwed, for example, into a vertebra. The head 11 of this screw, which projects out of the vertebra, has a spherical shape. The upper surface of the ball head 11 is flattened. In this region a hexagon socket (not shown here) is provided, into which a complementary tool can be inserted in order to screw the pedicle screw into the vertebra.

The head 11 of the pedicle screw 10 comprises a passage in the form of a bore 12 passing all the way through the head and having at each end an entrance or exit opening 13, 14 that expands conically outward. Within the bore 12 is placed a cable- or wire-like tensioning means 15, to which after implantation a pulling force is applied. Spacer sleeves 16 are pushed over the tensioning means 15 in order to keep adjacent anchoring elements, in this case pedicle screws 10, a predetermined distance apart when a pulling force is applied to the cable- or wire-like tensioning means 15. The spacer sleeves 16 are braced against the spherical surface of the screw head 11. The end faces 17 of the spacer sleeves 16 that are apposed to the ball head 11 of the pedicle screw 10 have a shape complementary to that of the spherical supporting surface; that is, they have a spherically concave shape. As a result, the spacer sleeves abut against the ball head 11 of the pedicle screw 10 over a relatively large area within a range of angles, indicated in the attached drawing by the double-headed curved arrow 18.

The angle at which the spacer sleeves 16 abut against the ball head 11 of the pedicle screw 10 corresponds to the angle at which the cable- or wire-like tensioning means 15 enters or emerges from the bore 12 in the ball head 11. The maximal entrance or exit angle of the tensioning means is specified by the conical structure of the entrance or exit opening 13, 14.

The passages 19 in the spacer sleeves 16 likewise comprise entrance or exit openings 20 that expand outward in a conical or trumpet-like shape, so as to ensure that in the region where the spacer sleeves 16 abut against the associated anchoring element, in this case against the ball head 11 of the pedicle screw 10, the cable- or wire-like tensioning means 15 can run unconstrained from the spacer sleeve 16 into the passage 12 through the anchoring element, here the ball head 11 of the pedicle screw 10, or conversely. This unconstrained transition is clearly discernible in the attached drawing. Instead of the pedicle screw 10 shown here, a pedicle hook can serve as anchoring element.

It can also be provided that the ball head 10 is so mounted as to be rotatable about the long axis 21 of the pedicle screw. This allows the operator still more degrees of freedom with respect to the orientation of tensioning means and spacer sleeves.

Insofar as supporting balls 22 are to be disposed between two adjacent spacer sleeves, these have a shape corresponding to that of the ball head 11 of the pedicle screw 10. In FIG. 2, a supporting ball 22 is positioned on the tensioning means 15 between two spacer sleeves 16.

In the embodiment illustrated here, the ball head 11 is constructed in one piece and is an integral component of the pedicle screw 10. For implantation, the screw is first screwed into the vertebra and so positioned that the passage 12 is correctly oriented. Then the cable- or wire-like tensioning means 15 is threaded through the passage, after which the spacer sleeves 16 are pushed onto the tensioning means. At one of its ends the tensioning means 15 has a thickened section that abuts against the passage 12 of the anchoring element situated at one end of the part of the spinal column to be stiffened, whereas at its other end the tensioning means comprises a threaded section onto which a tensioning nut can be screwed. This nut abuts against the anchoring element situated at the other end of the part of the spinal column to be stiffened, either directly or indirectly by way of a short spacer sleeve.

As tensioning means 15 a threaded rod can also be used, i.e. a rod with an external thread extending over its entire length. This embodiment offers the advantage that the length of the threaded rod can be individually adjusted, depending on the requirements at the site of implantation.

In order to avoid the above-mentioned threading of the tensioning means through the passage 12 of the anchoring element, here the ball head 11 of the pedicle screw 10, it can be provided either that the ball head 11 is constructed in two parts, so that the passage 12 can be opened over its entire length in order to insert the tensioning means 15, or that a longitudinal slot 24 is formed on the ball head 11 by way of which the tensioning means 15 can likewise be inserted into the passage 12. The tensioning means 15 in this embodiment is quasi hook into the passage 12. FIG. 3 shows the anchoring element 10, wherein the ball head 11 has a slot 24. FIG. 4 shows an embodiment of a supporting ball 22 in which the supporting ball 22 also has a slot 26.

All components are made of human-compatible material, in particular titanium or a titanium alloy. The tensioning means in a special embodiment can be constructed as a flexible cable, in particular a cable braided like a rope.

In the implanted state a pulling force is applied to the tensioning means 15—as mentioned above—while the spacer sleeves 16 are under pressure.

The apparatus described here is suitable not only for stiffening and/or correcting a part of the spinal column, but rather for stiffening and/or correcting skeletal structures or a bone fracture in general, in particular as part of an external fixation device or intramedullary nail. However, the described system is particularly well suited for the correction and/or stiffening of a part of the spinal column.

All the characteristics disclosed in the application documents are claimed as essential to the invention insofar as they are new to the state of the art, singly or in combination.

| LIST OF REFERENCE NUMERALS | |
| --- | --- |
| 10 | Pedicle screw |
| 11 | Screw head |
| 12 | Bore |
| 13 | Entrance opening |
| 14 | Exit opening |
| 15 | Tensioning means |
| 16 | Spacer sleeve |
| 17 | End face |
| 18 | Double-headed curved arrow |
| 19 | Passage |
| 20 | Entrance or exit opening |
| 21 | Long axis of pedicle screw |

What is claimed is:

1. An apparatus for supporting and correcting a skeletal structure comprising at least two anchoring elements for a connecting element that comprises an elongate tensioning means that can be fixed to the anchoring element and spacer sleeves that can be slid over the tensioning means in order to keep adjacent anchoring elements a predetermined distance apart when a pulling force is applied to the tensioning means, each anchoring element being attachable to a bone or vertebra, wherein surfaces of the anchoring elements against which the spacer sleeves abut are spherically curved and an end face at an end of each spacer sleeve towards the anchoring element has a shape complementary to an associated supporting surface of the anchoring element, wherein the anchoring element comprises a passage for the tensioning means, and wherein entrance and exit openings of the passage passing through the anchoring element each expand outward on all sides in a conical or trumpet-like shape.

2. The apparatus according to claim 1, wherein a head of the anchoring element, which projects from the bone or vertebra, is spherical in shape.

3. The apparatus according to claim 1, wherein the passage is accessible over its entire length by way of a slot so that the tensioning means can be inserted into the passage in a direction perpendicular to a long direction of the passage.

4. The apparatus according to claim 1, wherein the passage is openable over its entire length so that the tensioning means can be inserted into the passage in a direction perpendicular to a long direction of the passage.

5. The apparatus according to claim 3, wherein the anchoring element is so constructed that it can be taken apart in a region of the passage for the tensioning means.

6. The apparatus according to claim 3, wherein a head of the anchoring element is so constructed that it can be taken apart in a region of the passage for the tensioning means.

7. The apparatus according to claim 1, wherein passages in the spacer sleeves comprise entrance or exit openings that expand outward in a conical or trumpet-like shape, so as to ensure that in a region where the spacer sleeves abut against the associated anchoring element the tensioning means can run unconstrained form the spacer sleeve into the passage through the anchoring element and conversely.

8. The apparatus according to claim 1, further comprising supporting balls that can be placed onto the tensioning means each of which can be interposed between two spacer sleeves in order to enable changing of the separation distance by assembling a row of at least two spacer sleeves of the same or different length.

9. The apparatus according to claim 1, further comprising slotted, supporting balls that can be placed onto the tensioning means, each of which can be interposed between two spacer sleeves in order to enable changing of the separation distance by assembling a row of at least two spacer sleeves of the same or different length.

10. The apparatus according to claim 1, wherein the anchoring elements comprise pedicle screws.

11. The apparatus according to claim 10, wherein a ball-head of a ball-head screw has a passage extending perpendicular to a long axis of the pedicle screw.

12. The apparatus according to claim 11, wherein the passage is a bore for the tensioning means.

13. The apparatus according to claim 1, wherein a part of the anchoring element that anchors the tensioning means is so mounted that it can be rotated about an axis extending perpendicular to the longitudinal extent of the tensioning means, or about the long axis of the pedicle screw.

14. The apparatus according to claim 13, wherein the part of the anchoring element that anchors the tensioning means is a ball head of a ball-head pedicle screw.

15. The apparatus according to claim 1, wherein the elongate tensioning means has a shape selected from the group consisting of cable-shaped, wire-shaped, and rod-shaped.

16. An apparatus for supporting and correcting skeletal structure comprising:

a plurality of anchors having at least a portion defining a convex and approximately spherical outer surface with a passage therethrough;

a elongated connector fixable to at least two of said plurality of anchors;

at least one spacer sleeve slidable over said elongated connector to separate at least two of said plurality of anchors when a pulling force is applied to said elongated connector, wherein said spacer sleeve comprises at least one end face having a concave portion complementary to and abutting said convex and approximately spherical outer surface of said anchor, and wherein said passage through said anchor increases in diameter toward the entrance and exit openings of said passage on said outer surface.

17. An apparatus for supporting and correcting skeletal structure comprising:

a plurality of anchors having a passage defined therethrough;

a elongated connector fixable to at least two of said plurality of anchors within said passages in said anchors;

at least one spacer having a passage defined therethrough and also fixable to said elongated connector within said passage in said spacer so as to separate at least two of said plurality of anchors when a pulling force is applied to said elongated connector, wherein an end face of said spacer sleeve abuts said anchor, and wherein said passage through said anchor and said passage through said spacer both increase in diameter toward entrance and exit openings of said passages.

\* \* \* \* \*